US006743768B2

(12) United States Patent
Gautschi et al.

(10) Patent No.: US 6,743,768 B2
(45) Date of Patent: Jun. 1, 2004

(54) FRAGRANCE COMPOSITION COMPRISING A MIXTURE OF NITRILES

(75) Inventors: Markus Gautschi, Zeiningen (CH); Jean-Pierre Bachmann, Wädenswil (CH)

(73) Assignee: Givaudan SA, Vernier-Geneve (CH)

( * ) Notice: Subject to any disclaimer, the term of this patent is extended or adjusted under 35 U.S.C. 154(b) by 441 days.

(21) Appl. No.: 09/910,303

(22) Filed: Jul. 20, 2001

(65) Prior Publication Data

US 2002/0035054 A1 Mar. 21, 2002

(30) Foreign Application Priority Data

Jul. 21, 2000 (EP) .......... 00115699

(51) Int. Cl.[7] .......... A61K 7/46
(52) U.S. Cl. .......... 512/1; 512/6
(58) Field of Search .......... 512/6, 1

(56) References Cited

U.S. PATENT DOCUMENTS 3,325,369 A 6/1967 Somerville et al.
5,105,005 A 4/1992 Hopp et al.
5,888,962 A 3/1999 Frank et al.
5,892,092 A 4/1999 Kramer et al.

FOREIGN PATENT DOCUMENTS

WO WO 99/26601 6/1999

OTHER PUBLICATIONS

Zhu, L., et al., *J. Org. Chem.*, 56: 1445–53 (1991).

Miyaura, N., et al., *J. Am. Chem. Soc.*, 111: 314–21 (1989).

Adamczyk, M., et al., *Tetrahedron*, 55: 63–87 (1999).

Fritz, et al., *Quantitative Analytical Chemistry*, 4th. Edition, 240–282 (1979).

*Primary Examiner*—Jill Warden
*Assistant Examiner*—Monique T. Cole
(74) *Attorney, Agent, or Firm*—Norris, McLaughlin & Marcus

(57) ABSTRACT

The present invention relates to a fragrance composition containing a mixture of (9E)-undecenonitrile, (9Z)-undecenonitrile, and 10-undecenonitrile, which can be combined with additional fragrance ingredients, and which is useful in perfumery, and a process of preparing a scented consumer product using the composition.

21 Claims, No Drawings

FRAGRANCE COMPOSITION COMPRISING A MIXTURE OF NITRILES

FIELD OF THE INVENTION

The present invention relates to fragrance compositions containing a mixture of (9E)-undecenonitrile, (9Z)-undecenonitrile, and 10-undecenonitrile, to a process of providing a fragrance to a substrate using these compositions, and to a process for preparing scented consumer products containing the mixture.

BACKGROUND OF THE INVENTION

Aldehydes with hesperidic and floral notes are important perfumery ingredients. Examples of such aldehydes are, e.g., octanal, nonanal, decanal, undecanal, 10-undecanal, and citral. However, these aldehydes are readily chemically altered under oxidizing conditions or in solutions having a pH lower than 5 or higher than 9. Under these conditions the above mentioned aldehydes are chemically modified and therefore lose their fragrance characteristics and/or generate additional off notes.

Nitriles such as (9E)-undecenonitrile (1)

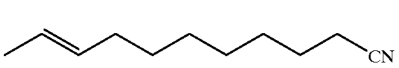

(1)

(9Z) -undecenonitrile (2)

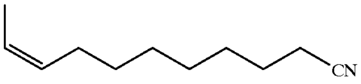

(2)

and 10-undecenonitrile (3)

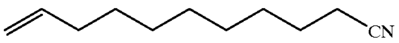

(3)

are described in the literature. Zhu et al. describe the synthesis of (9E)-undecenonitrile (1) by oxidative addition of functionalized organozinc compounds with allylic halide mediate (Zhu L. et al., *J. Org. Chem.* 1991, 56, 1445). In Adamczyk, M. et al., *Tetrahedron* 1999, 55, 63 (9Z)-undecenonitrile (2) has been described as an intermediate in the synthesis of pyridinoline. (Adamczyk, M. et al., *Tetrahedron* 1999, 55, 63). Miyaura et al. used 10-undecenonitrile (3) as the starting material for a palladium catalyzed cross coupling reaction (Miyaura, N. et al., *J. Am. Chem. Soc.* 1989, 111, 314). Further, a mixture of 3-methyl-5-phenyl-pentanenitrile and 3-methyl-5-cylcohexyl-pentanenitrile is disclosed in WO 99/26601.

The use of other nitrites such as decanonitrile, dodecanonitrile, tetrahydrogeranonitrile, Geranonitrile (3,7-dimethyl-2,6-octadienenitrile) and LEMONILE® (3,7-dimethyl-2(3),6-nonadienenitrile) is known in perfumery. These compounds are less chemically altered under strong acid, basic, and/or oxidizing conditions than aldehydes, and they exhibit aldehydic and hesperidic notes with floral aspects which are similar to those of the above mentioned aldehydes. However, a harsh, metallic odor appears as concomitant of these nitrites, which confers a "synthetic" and "dirty, fatty" aspect to the compositions to which they are applied.

SUMMARY OF THE INVENTION

An object of the present invention is to provide a fragrance composition which has a fresh sparkling, floral, fruity, and warm odor and a high stability under aggressive alkaline conditions.

Another object of the present invention to provide a fragrance composition which has a fresh sparkling, floral, fruity, and warm odor and a high stability under aggressive acidic conditions.

It is further object of the present invention to provide a fragrance composition which has a fresh sparkling, floral, fruity, and warm odor and a high stability under aggressive oxidative conditions.

One embodiment of the present invention is a fragrance composition containing a mixture of (9E)-undecenonitrile, (9Z)-undecenonitrile, and 10-undecenonitrile.

Another embodiment of the present invention is a process for providing a fragrance to a substrate by contacting a substrate with a fragrance composition wherein the fragrance composition contains a mixture of:

(a) (9E)-undecenonitrile;

(b) (9Z)-undecenonitrile; and (c) 10-undecenonitrile.

A further embodiment of the present invention is a process for preparing a scented consumer product by:

combining a mixture of:
- i) (9E)-undecenonitrile,
- ii) (9Z)-undecenonitrile, and
- iii) 10-undecenonitrile with a base material for a consumer product.

DETAILED DESCRIPTION OF THE INVENTION

The present invention relates to a fragrance composition containing a mixture of (9E)-undecenonitrile, (9Z)-undecenonitrile, and 10-undecenonitrile.

It has been found that mixtures of (9E)-undecenonitrile, (9Z)-undecenonitrile, and 10-undecenonitrile have a well-balanced fresh, sparkling floral, fruity, and warm odor and do not have the typical greasy, fatty character of nitriles. These mixtures also exhibit a very nice natural and lactonic aspect which is new for nitrile compositions. Additionally, mixtures of the present invention exhibit an astonishing olfactory stability in hostile media. Mixtures of the present invention are characterized by their outstanding stability under neutral, aggressive acidic, alkaline, and/or oxidizing conditions, by their excellent diffusion and pleasant odor and especially by lacking the greasy, fatty character of other nitriles. In many aspects, the compositions of the present invention are better than the current benchmark compound decanonitrile and are therefore preferred.

The fragrance composition according to the present invention, may be used alone or in combination with numerous fragrance ingredients of natural and/or synthetic origin. The range of the natural fragrances includes in addition to volatile, also moderately and only slightly volatile components. Synthetic fragrance ingredients belong to practically all classes of fragrant substances. Examples of such natural and synthetic ingredients are listed e.g. in "perfume and Flavor Materials of Natural Origin," S. Arctander, Ed., Elizabeth, N.J., 1960 and "perfume and Flavor Chemicals," S. Arctander, Ed., Vol. I & II, Allured Publishing Corporation, Carol Stream, USA, 1994.

An additional fragrance ingredient can be added to the mixture of the fragrance composition according to the present invention. A fragrance ingredient is defined as a substance with olfactory characteristics. An additional fragrance ingredient may consist of one or more ingredients.

The compositions of the present invention harmonize particularly well with additional fragrance ingredients such as fresh, hesperidic notes (lemon, mandarin, etc.), fruity accords (peach, apricot, etc.), floral notes (lily of the valley, rose, iris, jasmine, ylang-ylang, narcissus notes, etc.), green and agrestic notes (galbanum, tagete, lavender, thyme, etc.).

(9E)-undecenonitrile is the major compound in the mixture of the fragrance composition according to the present invention, making up more than 30% by weight of the mixture. Preferably, the mixture is made up of between about 30% and about 80% by weight of (9E)-undecenonitrile, more preferably between about 40% and about 60% by weight. In a preferred embodiment, 10-undecenonitrile is the minor component in the mixture, making up less than 40% by weight of the mixture. Preferably, the mixture is made up of between about 0.01% and about 30% by weight, more preferably between 5% and 20% by weight, of 10-undecenonitrile.

Due to their excellent odor and application qualities, the compositions of the present invention are excellent for use in any field of perfumery, especially in functional perfumery. Consumer products with a non-hostile or a hostile media containing a fragrant composition according to the present invention, as well as an additional ingredient, are preferred. Consumer products with a non-hostile (neutral characteristics) media include alcoholic solutions, shampoos, hair conditioners, bath oils, air fresheners, cosmetics, and skin care products. Consumer products with aggressive alkaline media ("alkaline medium") include soaps, laundry detergents, bleaches, automatic dishwashing powders, and scouring powders. Consumer products with aggressive acidic media ("acidic medium") include fabric softeners, deodorants, antiperspirants, and cleaners containing citric acid, hydrochloric acid, sulfonic acid, or phosphoric acid. Consumer products with aggressive oxidizing media ("oxidizing medium") include hair colorants and bleaches.

As used herein, the term "neutral" means a pH of between about 5 and about 9; the term "aggressive acidic" means a pH of less than about 5; the term "aggressive alkaline" means a pH of greater than about 9; and the term "aggressive oxidizing" means oxidizing agents in liquid products (e.g., NoOCl (>1% ww active chlorine), $H_2O_2$ (>1% ww)), and/or oxidizing agents in solid products (e.g., perborate or percabonate (>5% ww)).

The amount of the fragrant compositions of the present invention in the product, alone or in combination with other fragrance ingredients, varies depending on the nature of the product, and the intensity of the desired odor. These factors are known to those skilled in the art. Preferably, the compositions of the present invention are present in the range of 0.01% to 1% in the product.

The compositions of the present invention can be used in a variety of cleansing products for household and commercial applications, including bleaches, laundry detergents, dishwasher detergents, stain removers, scouring agents, fabric softeners, soaps, and all purpose and special cleaners, in various forms including liquids, gels, sprays, bars, sticks, and powders.

As used herein, the term "substrate" means a fabric, a hard surface, skin, hair, or any other surface upon which it would be desirable to impart a fragrance.

The fragrance compositions according to the present invention can be obtained either by a one-pot reaction from a mixture of the corresponding aldehydes, or by mixing the purified nitrites (1)–(3), obtained from the pure corresponding aldehydes. It is not necessary, but it is possible, to purify the aldehyde mixture before starting the one-pot reaction.

The scented consumer products for functional perfumery are prepared by admixing the mixture of (9E)-undecenonitrile, (9Z)-undecenonitrile, and 10-undecenonitrile, other optional fragrance ingredients, and a base material, e.g., a consumer product containing liquid and/or solid ingredients and a medium.

The following examples are provided to further illustrate the process of the present invention. These examples are illustrative only and are not intended to limit the scope of the invention in any way.

EXAMPLES

Example 1

(E,Z)-9-Undecenonitrile a) (E,Z)-9-Undecanal Oxime

To a solution of hydroxylamine hydrochloride (125.2 g, 1.8 mol) and sodium acetate (118.0 g, 1.44 mol) in $H_2O$ (480 ml), Aldehyde Iso C11 ((E,Z)-9-undecanal (201.6 g, 1.2 mol) Givaudan SA, Vernier, Switzerland) is rapidly added. Then methanol (170 ml) is added to the mixture. The mixture is heated for 3 hours at 60° C., allowed to cool to room temperature, and diluted with hexane (600 ml). The organic solution is washed 1× with saturated $NaHCO_3$ solution (300 ml), 2× with $H_2O$ (500 ml each), dried over $MgSO_4$ and concentrated in vacuo to give a crystalline solid (225 g) which is directly used in the next step. Yield: quantitative b) (E,Z)-9-Undecenonitrile The reaction flask is charged with acetic anhydride (612 g, 6 mol) and heated to 120° C. A solution of (E,Z)-9-undecanal oxime (225 g, 1.2 mol) in toluene 890 mml is added slowly over a period of 2.5 hours. The reaction mixture is kept at reflux temperature for 4 hours, cooled to room temperature, and diluted with hexane (600 ml). The organic solution is washed 3× with $H_2O$ (800 ml each), 3× with 5N NaOH (300 ml each), and 3× with brine (600 ml each), dried over $MgSO_4$, and concentrated in vacuo to give a yellowish oil (217 g). Distillation over a 25 cm Widmer column (87° C./0.05 mbar) afforded (E,Z)-9-undecenonitrile (124.8 g; 63%, 2 steps) in the form of a colorless oil. The product contained (9E)-undecenonitrile: 56%, (9Z)-undecenonitrile: 26%, and 10-undecenonitrile: 8%.

$^1$H-NMR (400 MHz, $CDCl_3$): 1.22–1.40(m, 6H); 1.40–1.50 (m, 2H); 1.58–1.70 (m, 5H); 1.93–2.14 (m, 2H); 2.33 (t, J=7.1 Hz, 2H); 5.33–5.48 (m, 2H).

MS [m/z (EI)]: 165 ($M^+$, 1), 136 (48), 122 (61), 69 (41), 55 (100), 41 (56).

Example 2

Stability of the Perfumery Material of the Invention in Liquid Bleach

A mixture of the perfumery material of the invention, obtained according to example 1, was added at 0.15% (wt) to a liquid bleach solution composed of 5% by weight of sodium hypochlorite and 95% by weight of water, adjusted to a pH of about 11.5 to 12.0 by the addition of sodium hydroxide (sample I). A similar mixture was prepared with decanonitrile as control experiment (sample IV). The odor of each solution was then evaluated by a panel of 14 perfumers. Both solutions were then divided into two aliquots, which were stored for 1 month at 4° C. (samples II and V) and 37° C. (samples III and VI), respectively. All solutions were then again assessed olfactorily by a panel of 14 perfumers. Furthermore, the content of free chlorine was determined for all samples by titration, according to standard procedures known to a person skilled in the art, e.g., as described by Fritz et al., Quantitative Analytical Chemistry, 2$^{nd}$ Ed. (1969), 101–118, 239–284.

The data in the table below show that the tested mixture of the compounds of the invention is chemically acceptably stable as compared to the stability of the benchmark compound, decanonitrile. It is also clear from the data that the mixture is olfactorily stable and the odor is perceived much more strongly and the mixture is more diffusive than an equal amount of decanonitrile. All 14 perfumers preferred the solution comprising the mixture of the invention for being nicely citrusy, floral/fruity over decanonitrile which was perceived citrusy, greasy/fatty.

TABLE 1

Chemical Stability

| Sample | Composition | Active Chlorine Content [%] | | |
|---|---|---|---|---|
| | | fresh | 30d/0° C. | 30d/37° C. |
| I | mixt. of example 1, 0.15% | 4.04 | — | — |
| II | mixt. of example 1, 0.15% | — | 3.73 | — |
| III | mixt. of example 1, 0.15% | — | — | 2.82 |
| IV | decanonitrile, 0.15% | 4.02 | — | — |
| V | decanonitrile, 0.15% | — | 3.81 | — |
| VI | decanonitrile, 0.15% | — | — | 3.16 |

TABLE 2

Olfactory Stability

| Sample | Stability[1)] | Olfactory description | Bleach coverage |
|---|---|---|---|
| I | +++ | citrusy, floral/fruity | good, preferred over IV |
| II | +++ | citrusy, floral/fruity | good, preferred over V |
| III | +++ | citrusy, floral/fruity | good, preferred over VI |
| IV | +++ | citrusy, fatty/greasy | good, more greasy fatty than I |
| V | ++ | citrusy, fatty/greasy | good, more greasy fatty than II |
| VI | ++ | citrusy, fatty/greasy | good, more greasy fatty than III |

[1)]Olfactory Stability: +++ = stable; ++ = acceptably stable, slight change; + = unstable, not disagreeable; − = unstable, off-odor.

Example 3

Citrus Fragrance Composition for a Bleach Containing Consumer Product

| Ingredients | Percent weight (+) | Percent weight (−) |
|---|---|---|
| AGRUMEX ® | 14.0 | 14.0 |
| AMBERKETAL ®, 10% in IPM[1)] | 0.4 | 0.4 |
| AMBROFIX ®[1)] | 0.4 | 0.4 |
| CLONAL ® | 2.0 | 2.0 |
| Cumin nitrile | 0.1 | 0.1 |
| DAMASCONE ALPHA ®[2)] | 0.4 | 0.4 |
| Dihydromyrcenol | 25.0 | 25.0 |
| Diphenyl oxide | 10.0 | 10.0 |
| Dipropylene glycol | 24.0 | 25.0 |
| Ethyl vanilline[2)] | 0.4 | 0.4 |
| Eucalyptol | 3.0 | 3.0 |
| Fenchyl alcohol | 0.5 | 0.5 |
| FRUCTONE ® | 0.5 | 0.5 |
| IRISANTHEME ® | 2.0 | 2.0 |
| RHUBAFURAN ® | 0.5 | 0.5 |
| ROSALVA ® | 0.8 | 0.8 |
| Tetrahydro linalool | 15.0 | 15.0 |
| (E,Z)-9-undecenonitrile[3)] | 1.0 | 0 |
| Total | 100 | 100 |

[1)]at 10% in MIP.
[2)]at 10% in DPG.
[3)]Mixture prepared as described in example 1.

| Tradename | Generic Name | Manufacturer |
|---|---|---|
| AGRUMEX ® | 2-tert.butylcyclohexyl acetate | H & R |
| AMBERKETAL ®, 10% In IPM | 5H-3,5a-epoxynaphthl[2,1-c]oxepin,dodecahydro-3,8,8,11a-tetramethyl- | Givaudan |
| AMBROFIX ® | 3a,6,6,9a-tetramethyl-dodecahydronaphtho [2,1-b]furan | Givaudan |
| CLONAL ® | dodecane nitrile | IFF |
| DAMASCONE ALPHA ® | 1-(2,6,6-trimethyl-2-cyclohexen-1-y1)-2-buten-1-one | Firmenich |
| FRUCTONE ® | ethyl 2-methyl-1,3-dioxolane-2-acetate | IFF |
| IRISANTHEME ® | alpha-isomethylionone | Givaudan |
| RHUBAFURAN ® | 2,4-dimethyl-4-phenyltetrahydrofuran | Quest |
| ROSALVA ® | 9-decenol-1 | IFF |

The listed manufacturers are as follows: “Firmenich” is Firmenich (International) SA (Geneva, Switzerland), “Givaudan” is Givaudan SA (Vernier, Switzerland), “H & R” is Haarmann & Reimer (Holzminden, Germany), “IFF” is IFF: International Flavors & Fragrances Inc. (New York, N.Y., USA), and “Quest” is Quest International Inc. (Mount Olive, N.J., USA).

The presence of (E,Z)-9-undecenonitrile with its fresh, sparkling floral, fruity, and warm odor gives richness, volume, and strong diffusion power to the fragrance. It nicely promotes the rosy note of this accord, and adds a touch of a fruity/peach aspect. Its character is reminiscent of “Aldehyde Iso C11,” and makes the fragrance more perfumistic in the classical “Floral Aldehydic” tradition.

The invention being thus described, it will be obvious that the same may be varied in many ways. Such variations are not to be regarded as a departure from the spirit and scope of the invention and all such modifications are intended to be included within the scope of the following claims.

What is claimed is:

1. A fragrance composition comprising a mixture of (9E)-undecenonitrile, (9Z)-undecenonitrile, and 10-undecenonitrile.

2. A fragrance composition according to claim 1 further comprising an additional fragrance ingredient.

3. A fragrance composition according to claim 2 wherein the additional fragrance ingredient has fresh hesperidic notes.

4. A fragrance composition according to claim 2 wherein the additional fragrance ingredient has fruity accords.

5. A fragrance composition according to claim 2 wherein the additional fragrance ingredient has floral notes.

6. A fragrance composition according to claim 2 wherein the additional fragrance ingredient has green and agrestic notes.

7. A fragrance composition according to claim 1 wherein the mixture has at least about 30% by weight of (9E)-undecenonitrile.

8. A fragrance composition according to claim 1 wherein the mixture has from about 40% to about 60% by weight of (9E)-undecenonitrile.

9. A fragrance composition according to claim 1 wherein the mixture has less than about 40% by weight of 10-undecenonitrile.

10. A fragrance composition according to claim 1 wherein the mixture has from about 0.01% to about 30% by weight of 10-undecenonitrile.

11. A fragrance composition according to claim 1 wherein the mixture has from about 5% to about 20% by weight of 10-undecenonitrile.

12. A consumer product comprising a fragrance composition according to claim 1.

13. A consumer product comprising a fragrance composition according to claim 1 in a neutral media.

14. A consumer product comprising a fragrance composition according to claim 1 in an acidic media.

15. A consumer product comprising a fragrance composition according to claim 1 in an oxidizing media.

16. A consumer product comprising a fragrance composition according to claim 1 in an alkaline media.

17. A consumer product comprising a fragrance composition according to claim 1 in an amount from about 0.01% to about 1% by weight.

18. A process for providing a fragrance to a substrate comprising contacting a substrate with a fragrance composition comprising a mixture of:

i) (9E)-undecenonitrile, ii) (9Z)-undecenonitrile, and iii) 10-undecenonitrile.

19. A process according to claim 18 wherein the fragrance composition further comprises an additional fragrance ingredient selected from the group consisting of a fragrance ingredient having hesperidic notes, a fragrance ingredient having fruity accords, a fragrance ingredient having floral accords, a fragrance ingredient having green and agrestic notes, and combinations thereof.

20. A process for preparing a scented consumer product comprising:

combining a mixture of:

i) (9E)-undecenonitrile, ii) (9Z)-undecenonitrile, and iii) 10-undecenonitrile with a base material for a consumer product.

21. A process according to claim 20 further comprising the step of admixing an additional fragrance ingredient into the mixture.

* * * * *